US00PP15698P2

(12) United States Plant Patent
Bergman

(10) Patent No.: US PP15,698 P2
(45) Date of Patent: Mar. 22, 2005

(54) ***CHRYSANTHEMUM* PLANT NAMED 'YONEW YORK'**

(50) Latin Name: *Chrysanthemum×morifolium*
Varietal Denomination: Yonew York

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/786,926

(22) Filed: Feb. 25, 2004

(51) Int. Cl.[7] ..... A01H 5/00
(52) U.S. Cl. ..... Plt./287; Plt./288; Plt./291
(58) Field of Search ..... Plt./287, 288, 291

(56) References Cited

U.S. PATENT DOCUMENTS

PP8,936 P * 10/1994 VandenBerg ..... Plt./291
PP13,896 P3 * 6/2003 Bergman ..... Plt./291
2002/0092068 P1 * 7/2002 Vandenberg ..... Plt./291

OTHER PUBLICATIONS

UPOV ROM GTITM Computer Database, GTI Jouve Retrieval Software 2004/04 Citations for 'Yonew York'.*

* cited by examiner

*Primary Examiner*—Kent Bell
*Assistant Examiner*—W C Haas
(74) *Attorney, Agent, or Firm*—C. A. Whealy

(57) ABSTRACT

A new and distinct cultivar of *Chrysanthemum* plant named 'Yonew York', characterized by its uniform and outwardly spreading plant habit; strong and freely branching growth habit; dark green-colored foliage; uniform flowering response and habit; can be grown as a disbud or spray-type; early flowering habit; decorative-type inflorescences; light pink-colored ray florets; and good postproduction longevity with plants maintaining good substance and color for about three to four weeks in an interior environment.

2 Drawing Sheets

Botanical classification/cultivar designation: *Chrysanthemum×morifolium* cultivar Yonew York.

BACKGROUND OF THE INVENTION

The present Invention relates to a new and distinct cultivar of *Chrysanthemum* plant, botanically known as *Chrysanthemum×morifolium* and herein referred to by the name 'Yonew York'.

The new *Chrysanthemum* is a product of a planned breeding program conducted by the Inventor in Salinas, Calif. and Fort Myers, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* originated from a cross-pollination made by the Inventor in February, 2000, in Salinas, Calif., of a proprietary *Chrysanthemum* seedling selection identified as code number YB-6277, not patented, as the female, or seed, parent with a proprietary *Chrysanthemum* seedling identified as code number YB-4934, not patented, as the male, or pollen, parent. The new *Chrysanthemum* was discovered and selected by the Inventor in November, 2000, as a single flowering plant from within the resulting progeny of the stated cross-pollination grown in a controlled environment in Fort Myers, Fla.

The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new *Chrysanthemum* by vegetative tip cuttings was first conducted in Fort Myers, Fla. in February, 2001. Asexual reproduction by cuttings has shown that the unique features of this new *Chrysanthemum* are stable and reproduced true to type in successive generations.

SUMMARY OF THE INVENTION

The cultivar Yonew York has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yonew York'. These characteristics in combination distinguish 'Yonew York' as a new and distinct *Chrysanthemum:*

1. Uniform and outwardly spreading plant habit.
2. Strong and freely branching growth habit.
3. Dark green-colored foliage.
4. Uniform flowering response and habit.
5. Can be grown as a disbud or spray-type, but typically grown as a spray-type.
6. Early flowering, eight week response time.
7. Decorative-type inflorescences.
8. Light pink-colored ray florets.
9. Good postproduction longevity with plants maintaining good substance and color for about three to four weeks in an interior environment.

Plants of the new *Chrysanthemum* can be compared to plants of the female parent selection. Plants of the new *Chrysanthemum* differ from plants of the female parent selection primarily in plant growth habit as plants of the female parent selection are not as outwardly spreading as plants of the new *Chrysanthemum*. In addition, inflorescences of plants of the new *Chrysanthemum* flower have disc florets whereas inflorescences of plants of the female parent selection do not have disc florets.

Plants of the new *Chrysanthemum* can be compared to plants of the male parent selection. Plants of the new *Chrysanthemum* differ from plants of the male parent selection primarily in ray floret coloration as plants of the male parent selection have orange-colored ray florets.

Plants of the new *Chrysanthemum* can be compared to plants of the cultivar Yopresidio, disclosed in U.S. Plant Pat. No. 13,896. In side-by-side comparisons conducted in Fort Myers, Fla., plants of the new *Chrysanthemum* differed from plants of the cultivar Yopresidio in the following characteristics:

1. Plants of the new *Chrysanthemum* were shorter and more outwardly spreading than plants of the cultivar Yopresidio.
2. Inflorescences of plants of the new *Chrysanthemum* had disc florets whereas inflorescences of plants of the cultivar Yopresidio did not have disc florets.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum*.

The photograph on the first sheet comprises a side perspective view of typical flowering plants of 'Yonew York' grown as a spray-type.

The photograph on the second sheet comprises a close-up view of typical inflorescences of 'Yonew York' grown as a spray-type.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the winter in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yonew York.

Commercial classification: Decorative-type potted *Chrysanthemum*.

Parentage:

*Female, or seed, parent.*—Proprietary *Chrysanthemum×morifolium* seedling selection identified as code number YB-6277, not patented.

*Male, or pollen, parent.*—Proprietary *Chrysanthemum×morifolium* seedling selection identified as code number YB-4934, not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching.

Plant description:

*Appearance.*—Herbaceous decorative-type potted *Chrysanthemum* that can be grown as a spray or as a disbud-type, but typically grown as a spray-type. Upright with lateral branches outwardly spreading; uniformly mounded crown. Strong and freely branching growth habit; about three or four lateral branches develop after removal of terminal apex (pinching); dense and full plants.

*Plant height.*—About 26 cm.

*Plant width.*—About 39 cm.

*Lateral branches.*—Length: About 21 cm. Diameter: About 5 mm. Internode length: About 1.5 cm. Strength: Strong. Texture: Pubescent. Color: Close to 144A.

*Foliage description.*—Arrangement: Alternate; simple. Length: About 7.2 cm. Width: About 5.1 cm. Apex: Mucronate. Base: Truncate. Margin: Palmately lobed, sinuses between lateral lobes mostly parallel. Texture, upper and lower surfaces: Pubescent. Color: Developing and fully expanded foliage, lower surface: Close to 147A. Developing and fully expanded foliage, upper surface: Close to 147B. Venation, upper surface: Close to 147A to 147B. Venation, lower surface: Close to 147B. Petiole length: About 2.3 cm. Petiole diameter: About 3.5 mm. Petiole color, upper surface: Close to 146A. Petiole color, lower surface: Close to 146A to 146B. Petiole texture: Smooth.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences not fragrant. Plants can be grown as a spray or as a disbud-type, but typically grown as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about three to four weeks in an interior environment.

*Quantity of inflorescences.*—About six inflorescences develop per lateral branch.

*Inflorescence bud.*—Height: About 7 mm. Diameter: About 8 mm. Shape: Oblate. Color: Between 144A and 146A.

*Inflorescence diameter.*—About 6.4 cm.

*Inflorescence depth (height).*—About 2.5 cm.

*Diameter of disc.*—About 7.5 cm.

*Receptacle diameter.*—About 6.5 mm.

*Ray florets.*—Shape: Elongated oblong. Orientation: Initially upright, then perpendicular to the peduncle. Aspect: Straight, concave. Length: About 3.1 cm. Corolla tube length: About 5 mm. Width: About 1.1 cm. Apex: Emarginate, acute or rounded. Base: Fused into a corolla tube. Margin: Entire. Texture: Smooth, glabrous, satiny. Number of ray florets per inflorescence: About 101 arranged in numerous whorls. Color: When opening, upper surface: Close to 155D overlain with close to 77A. When opening, lower surface: Close to 155D underlain with close to 77A. Fully opened, upper surface: Close to 155D faintly overlain with close to 77A; color becoming closer to 155D with development. Fully opened, lower surface: Close to 155D faintly underlain with close to 77A; color becoming closer to 155D with development.

*Disc florets.*—Arrangement: Massed at center of receptacle. Shape: Tubular, elongated. Apex: Five-pointed. Length: About 8 mm. Diameter, apex: About 2 mm. Diameter, base: About 1 mm. Number of disc florets per inflorescence: About 45. Color: Immature: Close to 151A. Mature: Apex: Close to 9A. Mid-section and base: Close to 155D.

*Phyllaries.*—Quantity per inflorescence: About 16. Length: About 8 mm. Width: About 4 mm. Shape: Deltoid. Apex: Acute. Base: Truncate. Margin: Entire. Texture, upper surface: Waxy, smooth. Texture, lower surface: Pubescent. Color, upper surface: Close to 146A. Color, lower surface: Between 144A and 146A.

*Peduncles.*—Length: First peduncle: About 3.7 cm. Fourth peduncle: About 6.4 cm. Diameter: About 2.5 mm. Angle to vertical: About 45° from vertical. Strength: Strong, flexible. Texture: Pubescent. Color: Close to 144A.

*Reproductive organs.*—Androecium: Present on disc florets only. Anther color: Close to 12A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yonew York', as illustrated and described.

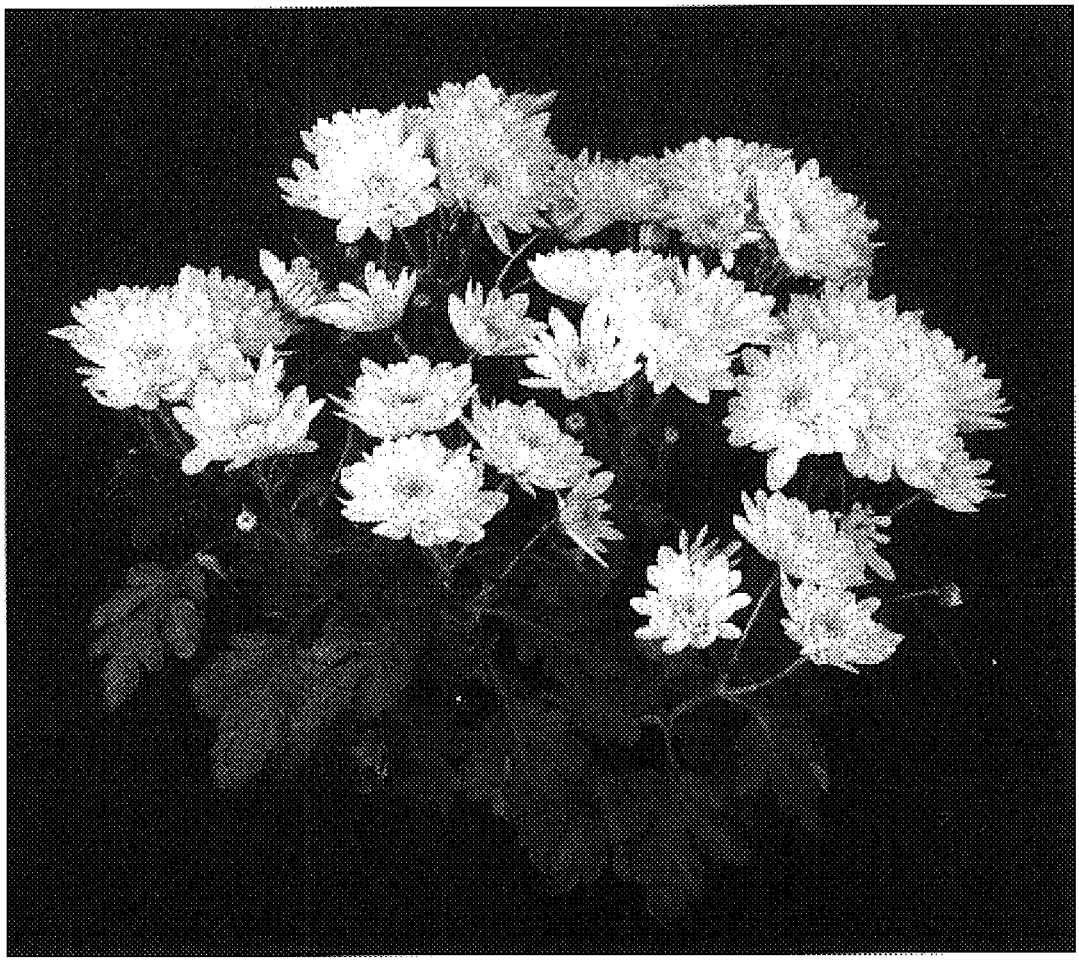

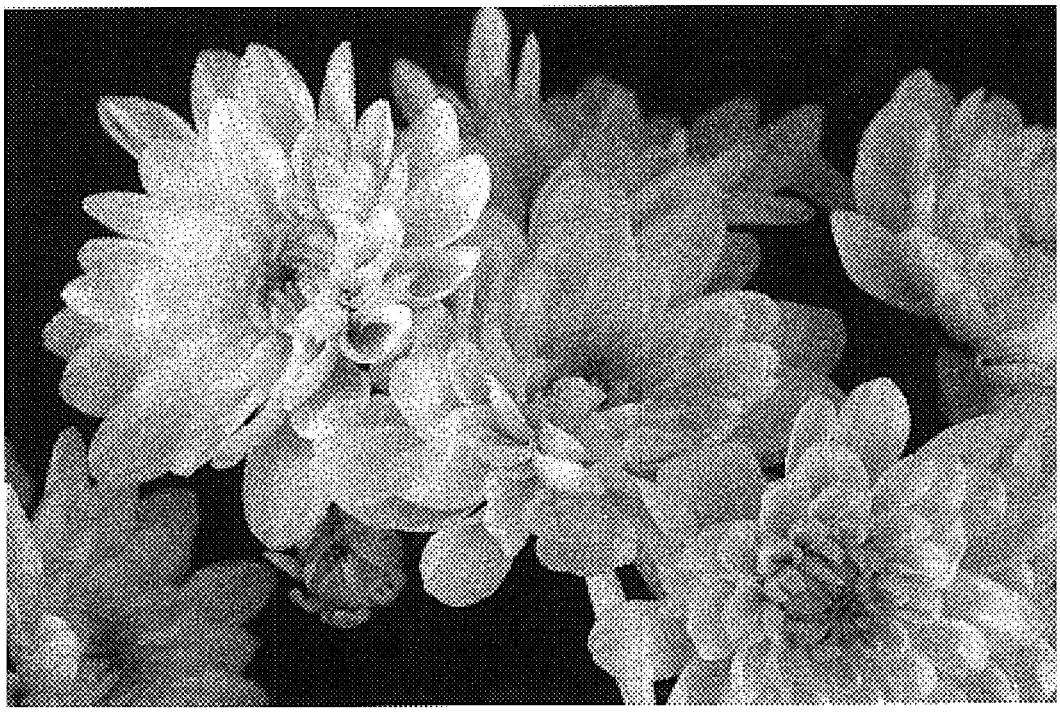

* * * * *